US005994323A

United States Patent [19]
Gerolymatos

[11] Patent Number: 5,994,323
[45] Date of Patent: Nov. 30, 1999

[54] PHARMACEUTICAL COMPOSITIONS COMPRISING CLIOQUINOL IN COMBINATION WITH VITAMIN B12 AND THERAPEUTIC AND PROPHYLACTIC USES THEREOF

[75] Inventor: Panayotis N. Gerolymatos, Kryoneri Attikis, Greece

[73] Assignee: P.N. Gerolymatos S.A., Kryoneri Attikis, Greece

[21] Appl. No.: 09/023,542

[22] Filed: Feb. 13, 1998

[30] Foreign Application Priority Data

Dec. 31, 1997 [GR] Greece ................................. 970100507

[51] Int. Cl.$^6$ .......................... A61K 31/70; A61K 31/44; A61K 31/47
[52] U.S. Cl. ............................ 514/52; 514/305; 514/306; 514/308
[58] Field of Search .............................. 514/52, 305, 306, 514/308

[56] References Cited

U.S. PATENT DOCUMENTS

| | | | |
|---|---|---|---|
| 3,574,819 | 4/1971 | Gross et al. ................................ | 424/21 |
| 5,286,492 | 2/1994 | Dettmar et al. ........................... | 424/458 |
| 5,373,021 | 12/1994 | Marangos .................................. | 514/483 |
| 5,505,958 | 4/1996 | Bello et al. ............................... | 424/449 |
| 5,607,691 | 3/1997 | Hale et al. ................................ | 424/449 |

FOREIGN PATENT DOCUMENTS

| | | |
|---|---|---|
| 3932338 | 4/1991 | Germany . |
| WO 92/18111 | 10/1992 | WIPO . |
| WO 93/10459 | 5/1993 | WIPO . |
| WO 95/19178 | 7/1995 | WIPO . |
| WO 95/31199 | 11/1995 | WIPO . |

OTHER PUBLICATIONS

"Idosyncratic Neurotoxicity: Clioquinol and Bismuth," 1980, *The Lancet* p. 857–858.
Baumgartner et al., 1979, Neurotoxicity of halogenated hydroxyquinolines: clinical analysis of cases reported outside Japan, *Journal of Neurology, Neurosurgery, and Psychiatry* 42:1073–1083.
Beppu, H., 1973, "Toxicity of Clioquinol (5–chloro–7–iodo—8–hydroxy–quinoline) on chick embryo dorsal root ganglia in tissue culture," 13:551–560 (w/English abstract).
Borg–Neczak et al., 1994, "Effect of 8–Hydroxy–,8–Mercapto– and 5–Chlorol–7–iodo–8–hydroxy–quinoline on the Uptake and Distribution of Nickel in Mice," *Pharmacology & Toxicology* 74:185–192.
Bush et al., 1994, "Rapid Induction of Alzheimer Aβ Amyloid Formation by Zinc," *Science* 265:1464–1467.
Bush et al., 1995, "The Role of Zinc in the Cerebral Deposition of Aγ Amyloid in Alzheimer's Disease," *Amyloidogenesis* pp. 607–618.
Bush et al., 1995, "Zinc and Alzheimer's Disease," *Science* 268:1921–1923.

Chaiyabutr et al., 1985, "Urinary Bladder Effects After Oral Dosages of the ntidiarrhoeal Drug (Clioquinol/Phanquinone/Oxyphenonium Bromide) in Experimental Drugs," *J. Med. Ass. Thailand* 68(12):649–653.
Committee on Drugs, "Blindness and Neuropathy From Diiodohydroxyquin–Like Drugs," American Academy of Pediatrics, p. 378–379 (1990).
Crapper McLachlan et al., 1991, Intramuscular and desferrioxamine in patients with Alzheimer's disease, *The Lancet* 337:1304–1308.
Degen et al., 1979, "Percutaneous Absorption of Clioquinol (Vioform®)," *Dermatologica* 159:295–301.
Esler et al., 1996, "Zinc–Induced Aggregation of Human and Rat β–Amyloid Peptides in Vitro," *Jounral of Neurochemistry* 66:723–732.
Fitzgerald, 1995, "Zinc and Alhzeimer's Disease, " *Science* 268:1920–1923.
Goto et al., 1982, "Impairment of Visual System of Beagles Orally Ingesting Clioquinol," *The Journal of Toxicological Sciences,* 7:19–25.
Goto et al., 1982, "Deterioration of Spinal Reflex in Beagles Orally Ingesting Clioquinol," *The Journal of Toxicological Sciences* 7:12.
Holtzman et al., 1996, "Developmental abnormalities and age–related neurodegeneration in a mouse model on Down Syndrome," *Proc. Natl. Acad. Sci. USA* 93:13333–13338.
Hori et al., 1987, "5–Chloro–7–Iodo–8–Hydroxyquinoline (Clioquinol) Inhibits The Nerve Growth Factor–Induced Stimulation Of RNA Synthesis In Neonatal Rat Superior Cervical Ganglion, In Vitro," *The Journal of Toxicological Sciences* 12:97–109.
Jack et al., 1973, "Pharmacokinetics of Iodochlorhydroxyquin in Man," *Journal of Pharmaceutical Sciences* 62(12):1929–1932.
Kaiser, 1994, "Alzheimer's : Could Thre Be a Zinc Link?," *Science* 265:1365.
Kawahara et al., 1997, "Alzheimer's Disease Amyloid β–Protein Forms $Zn^{2+}$–Sensitive, Cation–Selective Channels Across Excised Membrane Patches from Hypothalamic Neurons," *Biophysical Journal* 73:67–75.
Kirschner et al., 1987, "Synthetic peptide homologous to β protein from Alzheimer disease forms amyloid–like fibrils in vitro," *Proc. Natl. Acad. Sci. USA* 84:6953–6957.
Kono, R., 1975, "Introductory Review Of Subacute Myelo–Optico–Neuropathy (SMON) And Its Studies Done By The SMON Research Commission," *Japan J. Med. Sci. Biol.* 28:1–21.
Kotaki et al., 1983, "Intestinal Absorption and Metagolism of Clioquinol in the Rat," *J. Pharm. Dyn.* 6:881–887.

(List continued on next page.)

*Primary Examiner*—Theodore J. Criares
*Attorney, Agent, or Firm*—Pennie & Edmonds LLP

[57] ABSTRACT

A pharmaceutical composition is disclosed that comprises clioquinol, vitamin $B_{12}$, and, optionally, pharmaceutical acceptable carriers and/or excipients. The use of the pharmaceutical composition removes or alleviates the side effects of clioquinol.

33 Claims, 5 Drawing Sheets

OTHER PUBLICATIONS

Koyama ete al., 1989, "Electrophysiological changes in the fasciculus gracilus of the cat following chronic clioquinol administration," *Journal of the Neurological Sciences* 94:271–282.

LaFerla et al., 1996, "Extracellular Deposition of β–Amyloid upon p53–dependent Neuronal Cell Death in Transgenic Mice," *J. Clin. Invest.* 98(7):1626–1632.

Meade, T.W., 1975, "Subacute myelo–optic neuropathy and clioquinol," *Brit. J. prev. soc. Med.* 29:157–169.

Mumenthaler et al., 1979, "Transient global amnesia after clioquinol," *Journal of Neurology, Neurosurgery, and Psychiatry* 42:1084–1090.

Muratov et al., 1983, "Interaction of Voltaren and some Pyrazolone and Aniline Derivatives with Endoperoxide Prostaglandin Synthetase," pp. 44–46 (w/English abstract).

Nakae et al., 1972, "Relation between Subacute Myelooptic Neuropathy (S.M.O.N.) and Clioquinol: Nationwide Survey," *The Lancet* pp. 171–173.

Oakley, Jr., G.P., 1973, "The Neurotoxicity of the Halogenated Hydroxyquinolines," *JAMA* 225(4):395–397.

Oguro, 1974, "The interference of the water–soluble organic compounds in atomic absorption spectrophotometry of calcium," *Japan Analyst* pp. 1375–1378.

Okada et al., 1984, "Effects Of Metal–Containing Drugs Taken Simultaneously With Clioquinol Upon Clinical Features Of SMON," *the Journal of Toxicological Sciences* 9:327–341.

O'Mahony et al., 1995, "Bone Aluminium Content in Alzheimer's Disease," *Dementia* 6:69–72.

Ozawa et al., 1986, "Experimental Clioquinol Intoxication in Rats: Abnormalities in Optic Nerves and Small Nerve Cells of Dorsal Root Ganglia," *Acta Neuropathol (Berl)* 69:272–277.

Pericin, 1979, "Comparison of the Acute Toxicity of Clioquinol, Histamine, and Chloroform in Different Strains of Mice," *Arch. Toxicol.* Supple. 2:371–373.

Polites, 1996, "Transgenic model applications to drug discovery," *Int. J. Exp. Path.* 77:257–262.

Ricoy et al., 1982 "Subacute Myelo–Optic Neuropathy (SMON)," *Journal Of Sciences* 53:241–251.

Ross et al., 1997, "Zinc alters conformation and inhibits biological activities of nerve growth factor and related neurotrophins," *Nature Medicine* 3(8):872–878.

Sargeaunt et al., 1976, "In vitro sensitivity of *Entamoeba histolytica* to furazolidone and iodochlorhydroxyquin, separate and combined," *Transactions of the Royal Society of Tropical Medicine and Hygiene* 70(1):54–56.

Schmid et al., 1973, "Studies of the Distribution and Excretion of Clioquinol in the Animal," *Arzneim.–Forsch. (Drug Res.)* 23(11):1560–1566.

Shigematsu, I., 1975, "Subacute Myelo–Optico–Neuropathy (SMON) And Clioquinol," p. 35–54.

Shiraki, H., 1972, "The Neuropathology Of Subacute Myelo–Optico–Neuropathy, "SMON", In The Humans," p. 101–164.

Sobue et al., 1971, "Myeloneuropathy with abdominal disorders in Japan," *Neurology* 21:168–173.

Sobue, "Clinical aspects of subacute myelo–optico–neuropathy (SMON)," *Handbook of Clinical Neurology* 37:116–139 (1993).

Tamura et al., 1973, "Identification Of Green Pigment And analysis Of Clioquinol In Specimens From Patients With Subacute Myelo–Optico–Neuropathy," *Clinica Chimica Acta* 47:13–20.

Tamura, Z., 1975, "Clinical Chemistry of Clioquinol," p. 69–77.

Tateishi et al., 1975, "Experimental Reproduction of SMON in Animals by Prolonged Administration of Clioquinol: Clinoco–Pathological Findings" 28:165–186.

Thomas et al., 1984, "Correlated Nerve Conduction, Somatosensory Evoked Potential And Neuropathological Studies In Clioquinol And 2,5–Hexanedione Neurotoxicity In The Baboon," *Journal of the Neurological Sciences* 64:277–295.

Tsubaki et al., 1971, "Neurological Syndrome Associated with Clioquinol," *The Lancet* 696–697.

Wadia, 1984, "SMON as seen from Bombay," *Acta Neurol Scand* 70(suppl 100):159–164.

Weathersbee, A.A., 1943, "Observations On The Relative Attractiveness Of Man And Horse For Anopheles Albimanus Weideman," *The American Journal of Tropical Medicine* 14:25–33.

Weismann et al., 1978, "Effects of Penicillamine and Hydroxyquinoline on Absorption of Orally Ingested $^{65}$Zinc in the Rat," *The Journal of Investigative Dermatology* 71:242–244.

Wieniewski et al., 1996, "Some neuropathological aspects of Alzheimer's disease and its relevance to other desciplines," *Neuropathology and Applied Neurobiology* 22:3–11.

Wokes et al., 1955, "Human Dietary Deficiency of Vitamin $B_{12}$," *The American Journal of Clinical Mutrition* 3(5):375–382.

Yamanaka et al., 1973, "Uncoupling of Oxidative Phosphorylation of Rat Liver Mitochondira by Chinoform," *J. Biochem.* 73:993–998.

Yoshimura et al., 1992, "The Same Chemicals Induce Different Neurotoxicity When Administered in High Doses for Short Term or Low Doses for Long Term to Rats and Dogs," *Molecular and Chemical Neuropathology* 16:59–84.

Zaks et al., "Spasmolytic and Anti–Inflammatory Activity of 8–Hydroxyquinolines," p. 47 (English abstract) (1992).

PHARMACEUTICAL COMPOSITIONS COMPRISING CLIOQUINOL IN COMBINATION WITH VITAMIN B12 AND THERAPEUTIC AND PROPHYLACTIC USES THEREOF

TABLE OF CONTENTS
1. INTRODUCTION
2. BACKGROUND OF THE INVENTION
   2.1. CLIOQUINOL
   2.2. ALZHEIMER'S DISEASE
   2.3. PARKINSON'S DISEASE
3. SUMMARY OF THE INVENTION
4. BRIEF DESCRIPTION OF THE FIGURES
5. DETAILED DESCRIPTION OF THE INVENTION
   5.1. TREATMENT OF ALZHEIMER'S DISEASE
   5.2. TREATMENT OF PARKINSON'S DISEASE
   5.3. PHARMACEUTICAL COMPOSITIONS
6. EXAMPLES

1. INTRODUCTION

The present invention relates to a pharmaceutical composition comprising clioquinol and vitamin $B_{12}$ as well as the use of vitamin $B_{12}$ and clioquinol for the manufacture of a pharmaceutical composition for the treatment of a disorder that responds to clioquinol administration. The present invention is also directed to methods of treatment and prevention of disorders responsive to clioquinol administration, including but not limited to Alzheimer's disease, Parkinson's disease, *H. pylori* infections/ulcers, and other infectious diseases by administering both the chelating agent clioquinol and vitamin $B_{12}$. The use of vitamin $B_{12}$ in combination with clioquinol inhibits detrimental side effects of clioquinol administration.

2. BACKGROUND OF THE INVENTION

2.1. CLIOQUINOL

Clioquinol has been formulated and administered in various ways, at various doses (Ozawa et al., 1986, Acta Nueropathol (Berl) 69:272–277; Yamanaka et al., 1973, *J. Biochem.* 73:993–998; Sobue et al., 1971, *Neurology* 21:168–173; Tamura et al., 1973, *Clinica Chimica Acta.* 47:13–20; Jack and Riess, 1973, *J. Pharm. Sci.* 62(12):1929–1932; Baumgartner et al., 1979, *Journal of Neurology, Neurosurgery, and Psychiatry* 42:1073–1083, Kono, 1975, Japan. *J. Med. Sci. Biol.* 28:1–21; Sargeaunt and Lumsden, 1976, *Transactions of the Royal Society of Tropical medicine and Hygiene* 70(1):54–56; Nakae et al., 1973, Lancet 171–173; Mumenthaler et al., 1979, *Journal of Neurology, Neurosurgery, and Psychiatry* 42:1084–1090; Schmid et al., 1973, Arzneim.-Forsch. (*Drug Res.*) 23(11):1560–1566; Oakley, 1973, *JAMA* 225(4):395–397; David et al., 1943, *American J. Trop. Med.* 24:29–33; Thomas et al., 1984, *Journal of the Neurological Sciences* 64:277– 295; Yoshimura, 1992, *Molecular and Chemical Neuropathology* 16:59–84; Nakae, 1974, *Japan Public Health Journal* 15:607–611; Tateishi, 1973, *Japan Public Health Journal* 15:187–196; Degen et al., 1979, *Dermatologica* 159:295–301; Goto et al., 1982, *J. Toxicological Sciences* 7:1–12).

Clioquinol (5-chloro-7-iodo-8 hydroxyquinoline) was previously frequently used for the treatment of various disorders, such as amoebiasis and non-specific infectious diarrhea (Kono, 1975, *Japan J. Med. Sci. Biol.* 28:1–19, Meade, 1975, *Brit. J. Prev. Soc. Med.* 29:157–169). However, the use of clioquinol was stopped in Japan when the Japanese Government officially banned the sale in September 1970. The ban was motivated by the presumption that clioquinol caused subacute myelo-optico-neuropathy (SMON). Subsequently, clioquinol was withdrawn from the market in most other countries of the world on the recommendation of the World Health Organization. At present, clioquinol is only used topically due to its antibacterial and anti-fungal activity in skin infections.

SMON develops with an acute or subacute onset preceded by abdominal disorders and is characterized by dysesthesia of the legs, sensory disturbances, a variable degree of motor weakness, and visual loss. Corresponding to these clinical findings, SMON reveals pathologically symmetrical degeneration in peripheral nerves, spinal cord, posterior column, cardiac-spinal tract, and optic nerves.

The occurrence of SMON was confined to Japan even though clioquinol was prescribed world wide and not only in Japan. In the published literature no systematic pathological features resulting from the administration of clioquinol have been described other than the cases of SMON in Japan.

Although, in March 1972, the SMON Research Commission in Japan established a guideline for the treatment of SMON, wherein vitamin $B_{12}$ was recommended to be administered as part of a supply of various vitamins (*Jap. Med. Sci. Biol.* 28 *Suppl.* (1975)), it was never recognized that the deficiency of vitamin $B_{12}$, at least to some extent, might be responsible for SMON. Actually, the effect of vitamin $B_{12}$ in the treatment of SMON has been contested by Okuda, K. ("On vitamin $B_{12}$ metabolism in SMON patients years after the onset." Report of SMON Research Commission in 1972 (1973) 86), who reported that the vitamin $B_{12}$ level in the serum of SMON patients is normal. It was also observed that there may be pathological differences between SMON and $B_{12}$ deficiency. (Ricoy et al., 1982, *J. Neurol. Sci.* 53:241–251.) Hence, it was supposed that the administration of vitamin $B_{12}$ would not produce any improvement in the symptoms and signs of SMON.

After the withdrawal of clioquinol from the market there was a dramatic disappearance of new cases of SMON. At present, clioquinol is used topically due to its antibacterial and anti-fungal activity in skin infections.

Clioquinol has recently been shown to be effective in the treatment of *Heliocobacter pylori* (see International Publication No. WO 95/31199, dated Nov. 23, 1995) and neurotoxic injury (see International Publication No. WO 97/09976, dated Mar. 20, 1997 of Washington University).

The chelating ability of clioquinol is known for Fe, Co, Ni and Zn (Kidani et al., 1974, *Jap. Analyst* 23:1375–1378). Using mass spectrophotometry the coordination number for clioquinol for Co(II), Ni(II), Cu(II) and Zn(II) is 2, whereas the coordination number for Fe(III) is 3. Reportedly, injected preparations of clioquinol have crossed the blood-brain-barrier, leaving concentrations thereof in the brain on the order of 20 $\mu$l/ml when administered at dosages of 10–20 mg/kg (Tateishi et al., 1973, *Psychiat. Neurol. Jap.* 75:187–196 and Tamura, 1975, *Jap. J. Med. Sci. Biol. Suppl* 28:69–77). The concentration of clioquinol was also found to be high in such areas of the brain as the hippocampus.

Using microautoradiographic techniques, clioquinol has been shown in monkeys to form zinc chelates in the hippocampus. The Zn(II) chelates were mainly found in the terminal axodendritic boutons of the mossy fibres. Unconjugated clioquinol has an extremely rapid penetration into the nervous system when injected intravenously, with the ability to cross the blood-brain-barrier (Shiraki, 1979, In: Intoxications of the Nervous System. Part II. Handbook of Clinical Neurology, Vinken et al. eds., North Holland Publishing Co., New York, pp. 115–139).

Renewed interest has been evinced in clioquinol recently as it has been shown to be effective in the treatment of *Heliocobacter pylori* (see International Publication No. WO 95/31199, dated Nov. 23, 1995) and neurotoxic injury (see International Publication No. WO 97/09976, dated Mar. 20, 1997 of Washington University). In another filed, but not yet published, patent application, of the present applicant, clioquinol is disclosed to have activity in the treatment of Alzheimer's disease (PCT/IB97/00983, filed Aug. 8, 1997). Further, it is supposed that clioquinol has activity in the treatment of Parkinson's Disease. The aforementioned applications and publications are incorporated herein by reference in their entireties.

2.2. ALZHEIMER'S DISEASE

Alzheimer's disease (AD), which is the single major cause of dementia in adults in industrialized societies, is a degenerative brain disorder characterized clinically by a progressive loss of memory, confusion, dementia and ultimately death. Histopathologically, Alzheimer's disease is characterized by the presence in the neocortex, especially the hippocampus, of two brain lesions: the neurofibrillary tangles (NFTS) of paired helical filaments (PHF) in the neurons and the neuritic (senile) plaques in the extracellular space. The formation of senile plaques is related to the appearance of the symptoms and signs of the disease, including amnesia. After the formation of senile plaque, neurofibrillary tangles are produced in the neuronal bodies. The formation of neurofibrillary tangles is related to the worsening of amnesia and of the other symptoms of dementia.

A major component of the plaques are amyloid deposits, which are polypeptides referred to herein as Aβ (Amyloid-beta). The normal function of Aβ is not known at present but might be to form cation selective channels across cell membranes (Kawahara et al., 1997, *Biophysical Journal* 73/1, 67–75).

The precipitation of synthetic Aβ has been shown to be caused by several environmental factors including low pH, high salt concentrations and the presence of metals, e.g., zinc, copper, and mercury (Bush et al., 1995, *Science* 268:1921–1923). It has been reported that Aβ itself specifically and saturably binds zinc with a high affinity binding ($K_D$=107 nM) at a molar ratio of 1:1 (zinc: Aβ) (Bush et al., 1994, *J. Biol. Chem.* 269:12152–12158). This binding takes place at physiological concentrations of zinc (Bush et al., 1994, *Science* 265:1464–1467).

The chelating ability of clioquinol is known for Fe, Co, Ni and Zn (Kidani et al., 1974, *Jap. Analyst* 23:1375–1378). Using mass spectrophotometry the coordination number for clioquinol in case of Co(II), Ni(II), Cu(II) and Zn(II) is 2, whereas the coordination number for Fe(III) is 3. Reportedly, injected preparations of clioquinol have crossed the blood-brain-barrier, leaving concentrations thereof in the brain on the order of 20 µl/ml when administered at dosages of 10–20 mg/kg (Tateishi et al., 1973, *Psychiat. Neurol. Jap.* 75: 187–196 and Tamura, 1975, *Jap. J. Med. Sci. Biol. Suppl* 28:69–77). The concentration of clioquinol was also found to be high in such areas of the brain as the hippocampus.

2.3. PARKINSON'S DISEASE

In patients with typical Parkinson's disease (PD), the results of magnetic resonance imaging are usually normal. However, when a high field strength, heavily T2 weighed magnetic resonance imaging is used, a wider area of lucency in the substantia nigra is seen, indicative of increased accumulation of iron. In general, iron in the substantia nigra area has been reported in many publications as being causative of or at least contributing in the development of Parkinson's disease.

Iron is known to be a catalyst for the fenton reaction, by which the generation of reactive oxygen free radicals occurs. Iron is typically found within cells in the iron storage molecule ferritin. Once stored in ferritin, iron is unavailable as a catalyst for the production of free radicals.

Despite the enormous therapeutic advances, Parkinson's disease continues to be one of the most common causes of disability in the elderly. Research has been focused on the MPTP (1-methyl-4-phenyl-1,2,3,6-tetrahydropyridine toxin) model of Parkinson's disease based on the advances in the neuropathology and neurochemistry of the disease.

This toxin selectively damages the dopaminergic neurones of the substantia nigra when oxidized to MPP+. Anti-oxidants prevent the oxidation of MPTP to MPP+ and have been investigated clinically for the treatment of Parkinson's disease. It has been also postulated that endogenous or exogenous toxins, including metabolites of dopamine, generate hydroxyl radicals and hydrogen peroxide, which are known neurotoxic substances. These toxins interfere with normal mitochondrial metabolism. Abnormalities have also been reported in the complex I (NADH:ubiqinone oxidoreductase).

Citation or discussion of a reference hereinabove shall not be construed as an admission that such is prior art to the present invention.

3. SUMMARY OF THE INVENTION

According to the present invention a new pharmaceutical composition is provided, which comprises clioquinol, vitamin $B_{12}$ and, optionally, pharmaceutically acceptable carriers.

Also the use of vitamin $B_{12}$ and clioquinol for the manufacture of a pharmaceutical composition for the treatment or prevention of a disorder responding to clioquinol administration is suggested. Such disorders include, but are not limited to, Alzheimer's disease, Parkinson's disease, and bacterial, protozoal, viral or fungal infections, particularly bacterial infection caused by *Helicobacter pylori*.

Another object of the present invention is to provide methods of treating or preventing a disorder therapeutically responsive to clioquinol administration by administering a combination of clioquinol and vitamin B12. Such disorders include, but are not limited to, Alzheimer's disease, Parkinson's disease, and fungal, protozoal, viral or bacterial infection, including but not limited to bacterial infection caused by *Helicobacter pylori*.

The invention also provides methods of treating or preventing undesirable side effects of clioquinol administration by also administering to the subject receiving clioquinol, concurrently or sequentially, vitamin $B_{12}$.

5. DETAILED DESCRIPTION OF THE INVENTION

In view of the efficacy of clioquinol in therapy and prophylaxis of various diseases and disorders, there is a need to reintroduce clioquinol into the market. In this respect it is important to avoid the side effects of clioquinol administration, such as the symptoms and signs of SMON.

The relationship between SMON and clioquinol has been investigated and an explanation of the development of SMON as a consequence of clioquinol administration has been discovered. Thus, the object of the present invention is to remove or alleviate or prevent at least some of the side effects that occur when clioquinol is administered, whatever the reason for the administration may be. This object is achieved through the co-administration of vitamin $B_{12}$ with clioquinol.

In the following the invention will be explained in further detail. The proposed mechanism of action of the invention is not intended to limit the invention to said mechanism.

It is known that clioquinol is excreted through the kidneys as glucuronide or sulfate derivatives (Kotaki et al.: "Enterohepatic circulation of clioquinol in the rat", *J. Pharmacobiodyn.* 1984 June; 7(6):420–5 and Jurima et al.: "Metabolism of 14C-iodochlorhydroxy-quinoline in the dog and the rat", *J. Pharmacobiodyn.* 1984 March; 7(3):164–70), e.g., as the compound methyl (5-chloro-7-iodo-quinolyl-2',3',4'tri-O-acetyl-glucopyranosid)uronate. For short, this compound is referred to as clioquinol glucuronide in the following.

The detoxification of hydrophobic substances, such as clioquinol, in the body predominantly occurs in the liver. Therefore, it is believed that the clearance of clioquinol happens as follows: Clioquinol is converted to clioquinol glucuronide in the liver. Following the formation, the water soluble clioquinol glucuronide is secreted to the bile. The bile enters the intestine, wherein a major amount of the clioquinol glucuronide is evacuated in the stool. A certain amount of the clioquinol glucuronide is resorbed from the intestine to the blood. The clioquinol glucuronide is filtered from the blood in the kidneys and appears in the terminal urine.

By treating mice with clioquinol and subsequently administering a radioisotope of vitamin $B_{12}$ ([$^{57}$Co]-cyanocobalamine), it is shown in Example 1 below that the concentration of vitamin $B_{12}$ in the brain and the liver of the clioquinol-treated mice remains at a normal level, whereas the concentration of the radioisotope of vitamin $B_{12}$ is decreased in the kidney of such mice compared to the normal level. This finding suggests a metabolism of vitamin $B_{12}$ being dependent on clioquinol. Further, the finding suggests that the kidneys are the target organs, wherein the clioquinol dependent metabolism occurs.

In order to investigate a possible interaction between clioquinol glucuronide and vitamin $B_{12}$, an experiment was designed, wherein clioquinol glucuronide and vitamin $B_{12}$ were mixed in water. The mixture was analyzed by $^1$H NMR. The $^1$H NMR spectra, see FIGS. 1A–1C and 3B–3C, show that some of the resonances of vitamin $B_{12}$ (corresponding to the benzimidazole moiety) have shifted, and the same is observed for two resonances of the clioquinol glucuronide (corresponding to the quinoline moiety). It is believed by applicant that similar results would be expected using free clioquinol, however clioquinol cannot be dissolved in aqueous solutions for NMR testing.

The results indicate a hydrophobic interaction between clioquinol glucuronide and vitamin $B_{12}$, possibly between the benzimidazole moiety of the vitamin $B_{12}$ and the quinoline moiety of clioquinol glucuronide.

Vitamin $B_{12}$ is normally resorbed actively from the renal plasma after it has been filtered. In that way the body recovers most of the vitamin $B_{12}$ that would otherwise have been lost in the urine. It has recently been demonstrated that the resorption of vitamin $B_{12}$ is mediated by the action of the membrane protein megalin (Moestrup et al. *Proc. Natl. Acad. Sci.* 1996; 93(16):8612-7). The megalin is shown to have a strong affinity towards the binding of a complex formed by vitamin $B_{12}$ and the transport protein transcobalamin.

Based on the new finding reported herein, viz. that vitamin $B_{12}$ binds to clioquinol glucuronide, it is believed that vitamin $B_{12}$ does not bind to the megalin protein and/or the transcobalamin when it is already bound to the clioquinol glucuronide. Thus, the resorption of vitamin $B_{12}$ will fail and the body will suffer from vitamin $B_{12}$ deficiency after a certain time period of clioquinol administration if the body is not supplied with enough new vitamin $B_{12}$ through the normal diet.

Since the only source of vitamin $B_{12}$ is microorganisms, only microorganisms and species eating microorganisms contain vitamin $B_{12}$. Thus, diets low in meat and/or microorganisms will evidently cause vitamin $B_{12}$ deficiency. If persons are supplied with diets with a too low content of vitamin $B_{12}$, the administration of clioquinol will worsen the condition as the resorption of $B_{12}$ is prevented by the competitive binding of clioquinol with megalin. The fact that the Japanese diet in the 1960s predominantly consisted of vegetables and cereals, especially rice (Kromhout et al.: "Food consumption pattern in the 1960s in seven countries", *Am. J. Clin. Nutri.* 49:889–894, 1989), may explain why the SMON disease was confined to Japan.

The present invention solves the problem of clioquinol induced vitamin $B_{12}$ deficiency and the subsequent development of SMON by the co-administration of vitamin $B_{12}$ and clioquinol. Compositions, formulations, and kits for such co-administration are provided.

The invention also provides methods of treatment and/or prevention of disorders therapeutically or prophylactically responsive to clioquinol administration. Such disorders include but are not limited to infections (e.g., fungal infections, amoebiasis, bacterial infections (*Helicobacter pylori* infections, etc.), neurotoxic injury, infections resulting in peptic ulcer or infectious diarrhoea, Alzheimer's disease, and Parkinson's disease (see e.g., U.S. patent application Ser. Nos. to be assigned, respectively entitled "Clioquinol for the Treatment of Alzheimer's Disease" and "Clioquinol for the Treatment of Parkinson's Disease", by P. N. Gerolymatos, filed on even date herewith, each of which is incorporated by reference in its entirety).

By way of example, but not limitation, compositions and methods of the invention can be indicated for: 1) patients diagnosed with Alzheimer's disease or Parkinson's disease at any clinical stage of the disease, 2) the prevention of Alzheimer's disease or Parkinson's disease in patients with early or prodromal symptoms or signs, and 3) the delay of the onset or evolution or aggravation of the symptoms and signs of Alzheimer's disease or Parkinson's disease. The methods and compositions of the invention will be, for example, useful for the treatment of Alzheimer's disease or Parkinson's disease, the improvement or alleviation of any symptoms and signs of Alzheimer's disease or Parkinson's disease, the improvement of any pathological or laboratory findings of Alzheimer's disease or Parkinson's disease, the delay of the evolution of Alzheimer's disease or Parkinson's disease, the delay of onset of any Alzheimer's disease or Parkinson's disease symptoms and signs, the prevention of occurrence of Alzheimer's disease or Parkinson's disease, and the prevention of the onset of any of the symptoms and signs of Alzheimer's disease or Parkinson's disease.

The subject, or patient, is an animal, e.g., a mammal, and is preferably human, and can be a fetus, child, or adult.

5.1. TREATMENT OF ALZHEIMER'S DISEASE

In a specific embodiment, the invention provides a method of treating or preventing Alzheimer's disease with clioquinol in combination with vitamin $B_{12}$, administered concurrently or sequentially, thereby achieving therapeutic efficacy while inhibiting detrimental side effects of clioquinol administration. Clioquinol is believed to have the ability to penetrate the blood-brain barrier, to effectively chelate heavy metals to prevent the aggregation of amyloid, and to redissolve amyloid deposit. It could not have been predicted that clioquinol had the ability to redissolve zinc precipitated Aβ.

The following proposed mechanism of action of the invention is not intended to limit the invention to said mechanism. At present, applicant believes that clioquinol and Aβ competitively chelate zinc and other heavy metals. Clioquinol is regarded as the stronger chelator and will, therefore, predominately capture the heavy metal ions. Thus, zinc bound to Aβ in Aβ aggregates will be bound by clioquinol. The removal of zinc by clioquinol will resolubilize the Aβ protein. The complex of clioquinol and zinc should penetrate the blood-brain-barrier and be cleared from the organism.

The dose of clioquinol optimal in vivo for the resolubilisation of Aβ can be determined by a physician upon conducting routine experiments. An example of such an experiment is the monitoring of soluble Aβ in the cerebrospinal fluid (CSF) (WO 93/10459, dated May 27, 1993 of University of Melbourne). Beginning with relatively low doses (10–25 mg/day), a physician can monitor the amount of solubilized Aβ in a patient's CSF. If there is no increase in solubilized Aβ in response to the clioquinol administration, indicative of resolubilization of zinc-Aβ aggregates, the dosage can be raised until such an increase is observed.

Prior to administration to humans, the efficacy is preferably shown in animal models. Any animal model for Alzheimer's disease known in the art can be used.

5.2. TREATMENT OF PARKINSON'S DISEASE

In a specific embodiment, the invention provides a method of treating or preventing Parkinson's disease with clioquinol in combination with vitamin $B_{12}$, administered concurrently or sequentially, thereby achieving therapeutic efficacy while inhibiting detrimental side effects of clioquinol administration.

The invention provides a use of clioquinol and vitamin $B_{12}$ for the manufacture of a pharmaceutical composition for the treatment of Parkinson's disease. This composition is believed to have the ability to penetrate the blood-brain barrier, to effectively chelate heavy metals to prevent the generation of hydroxyl radicals and hydrogen peroxide, and to prevent oxidation of molecules found in the brain, including MPTP.

A role for an increase of oxidative stress in the mechanism of Parkinson's disease development is implicated by the finding that in all stages of Parkinson's disease, patients exhibit increased iron levels, decreased ferritin levels, and reduced glutathione (glutathione acts as a free radical scavenger by serving as a reducing agent).

Without intending to be bound by any mechanism, the aim of using a chelating agent such as clioquinol is to chelate or clear the iron that has been accumulated in the brain and, in particular, in the substantia nigra. In this way, iron catalyzed free radical production can be minimized and the oxidation of MPTP or other molecules inhibited.

Prior to administration to humans, the efficacy is preferably shown in animal models. Any animal model for Parkinson's disease known in the art can be used.

5.3. PHARMACEUTICAL COMPOSITIONS

The pharmaceutical compositions according to the present invention preferably comprise one or more pharmaceutically acceptable carriers and the active constituents. The carrier(s) must be "acceptable" in the sense of being compatible with the other ingredients of the composition and not deleterious to the recipient thereof. In a preferred embodiment, the clioquinol and/or vitamin $B_{12}$ in the pharmaceutical composition is purified.

It will be appreciated that the amounts of clioquinol and vitamin $B_{12}$ required for said treatment or prevention will vary according to the route of administration, the disorder to be treated, the condition, age, and file history of the subject, the galenic formulation of the pharmaceutical composition, etc.

Preferably, the clioquinol used in the invention is of high purity, such as that provided by Spectrum Quality Products, specification: USP 23; however any suitable preparation of clioquinol can be used in the methods and compositions of the invention.

Preferably, the vitamin $B_{12}$ used in the invention is of high purity, such as that provided by Hoffman La Roche, Ltd., specification: pharmaceutical grade; however any suitable preparation of vitamin $B_{12}$ can be used in the methods and compositions of the invention.

In general, a suitable (therapeutically effective) amount of clioquinol in the pharmaceutical composition is, for example, 5 to 250 mg, preferably 10 to 50 mg. A suitable amount of vitamin $B_{12}$, effective to inhibit clioquinol related side effects, in the pharmaceutical composition is, for example, 5 µg to 2 mg, preferably 0.5 to 1 mg. The actually administered amounts of clioquinol and vitamin $B_{12}$ may be decided by a supervising physician. Clioquinol and vitamin $B_{12}$ can be in the same composition for administering in combination concurrently, or in different compositions for administering concurrently but separately, or sequentially.

Therapeutic formulations include those suitable for parenteral (including intramuscular and intravenous), oral rectal or intradermal administration, although oral administration is the preferred route. Thus, the pharmaceutical composition may be formulated as tablets, pills, syrups, capsules, suppositories, formulations for transdermal application, powders, especially lyophilized powders for reconstitution with a carrier for intravenous administration, etc.

The term "carrier" refers to a diluent, adjuvant, excipient, or vehicle with which the therapeutic is administered. The carriers in the pharmaceutical composition may comprise a binder, such as microcrystalline cellulose, polyvinylpyrrolidone (polyvidone or povidone), gum tragacanth, gelatine, starch, lactose or lactose monohydrate; a disintegrating agent, such as alginic acid, maize starch and the like; a lubricant or surfactant, such as magnesium stearate, or sodium lauryl sulphate; a glidant, such as colloidal silicon dioxide; a sweetening agent, such as sucrose or saccharin; and/or a flavoring agent, such as peppermint, methyl salicylate, or orange flavoring.

Therapeutic formulations suitable for oral administration, e.g., tablets and pills, may be obtained by compression or molding, optionally with one or more accessory ingredients. Compressed tablets may be prepared by mixing clioquinol and vitamin $B_{12}$, and compressing this mixture in a suitable apparatus into tablets having a suitable size. Prior to the mixing, the clioquinol may be mixed with a binder, a lubricant, an inert diluent and/or a disintegrating agent and the vitamin $B_{12}$ may be mixed with a diluent, a lubricant and/or a surfactant.

In a preferred embodiment, free-flowing clioquinol powder is mixed with a binder, such as microcrystalline cellulose, and a surfactant, such as sodium lauryl sulphate until a homogeneous mixture is obtained. Subsequently, another binder, such as polyvidone, is transferred to the mixture under stirring. When a uniform distribution is obtained an aqueous solution of vitamin $B_{12}$ is added under constant stirring. This mixture is passed through granulating sieves and dried by desiccation before compression into tablets in a standard compressing apparatus.

In a second preferred embodiment, free-flowing clioquinol powder is mixed with surfactants and/or emulsifying agents, such as Sapamine® (N4'-stearoyl amino phenyl)-trimethylammonium methyl sulfuric acid) and lactose monohydrate until a uniform distribution of the constituents is obtained. A second preparation containing a disintegrating agent, such as maize starch, is added to the clioquinol mixture under continuous stirring. Such a second preparation may be prepared by adding excess boiling water to a maize starch suspended in cold water. An aqueous solution of vitamin $B_{12}$ is added to the clioquinol mixture. The final mixture is granulated and dried as above and mixed with maize starch and magnesium stearate and finally compressed into tablets in a standard apparatus.

A tablet may be coated or uncoated. An uncoated tablet may be scored. A coated tablet may be coated with sugar, shellac, film or other enteric coating agents.

Therapeutical formulations suitable for parenteral administration include sterile solutions or suspensions of the active constituents. An aqueous or oily carrier may be used. Such pharmaceutical carriers can be sterile liquids, such as water and oils, including those of petroleum, animal, vegetable or synthetic origin, such as peanut oil, soybean oil, mineral oil, sesame oil and the like. Formulations for parenteral administration also include a lyophilized powder comprising clioquinol and vitamin $B_{12}$ that is to be reconstituted by dissolving in a pharmaceutically acceptable carrier that dissolves vitamin $B_{12}$ and clioquinol, e.g., an aqueous solution of carboxymethylcellulose and lauryl sulfate.

When the pharmaceutical composition is a capsule, it may contain a liquid carrier, such as a fatty oil, e.g., cacao butter.

Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. These compositions can take the form of solutions, suspensions, emulsion, tablets, pills, capsules, powders, sustained-release formulations and the like. The composition can be formulated as a suppository, with traditional binders and carriers such as triglycerides.

In yet another embodiment, the therapeutic compound can be delivered in a controlled release system. In one embodiment, a pump may be used (see Langer, supra; Sefton, *CRC Crit. Ref. Biomed. Eng.* 14:201 (1987); Buchwald et al., *Surgery* 88:507 (1980); Saudek et al., *N. Engl. J. Med.* 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, *J. Macromol. Sci. Rev. Macromol. Chem.* 23:61 (1983); see also Levy et al., *Science* 228:190 (1985); During et al., *Ann. Neurol.* 25:351 (1989); Howard et al., *J. Neurosurg.* 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115–138 (1984)).

Other controlled release systems are discussed in the review by Langer (*Science* 249:1527–1533 (1990)).

In one embodiment of the pharmaceutical composition according to the invention, the active constituents, i.e., vitamin $B_{12}$ and clioquinol, are comprised as separate entities. The two entities comprising vitamin $B_{12}$ and clioquinol, respectively, may be administered simultaneously or sequentially. For example, clioquinol can be administered, followed by vitamin $B_{12}$ administered within a day, week, or month of clioquinol administration. If the two entities are administered sequentially, the entity comprising clioquinol is preferably administered for one to three weeks followed by a wash out period of one to four weeks during which the entity comprising vitamin $B_{12}$ is administered, but not the entity comprising clioquinol. After the wash out period, the treatment can be repeated.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

Other features and advantages of the invention will be apparent from the following examples, which in conjunction with the accompanying drawings illustrate by way of example the principles of the invention.

6. EXAMPLES

Example 1

The influence of clioquinol on vitamin $B_{12}$ in vivo was studied.

Six week old male mice were divided into two groups, a control group and a group which was injected with clioquinol(50 mg/kg/day). After three days, all of the mice were injected with [$^{57}$Co]-cyanocobalamine. After two days, the animals were sacrificed, and the brain, liver and kidney were dissected and counted in a gamma-counter as thousand cpm/g tissue (wet weight)±SEM. The radioactivities in each of the groups are stated in Table 1 below:

TABLE 1

| Treatment | Brain | Liver | Kidney |
|---|---|---|---|
| Control | 9.4 ± 0.9 | 97 ± 8 | 895 ± 207 |
| Clioquinol | 8.4 ± 1.5 | 85 ± 21 | 252 ± 61 |

A comparison of the results show that there were no significant changes in the amount of radioactivity accumulation in the brain and the liver. A reduction in the amount of vitamin $B_{12}$ trapped in the kidneys was apparent. This result suggests that clioquinol interferes with the vitamin $B_{12}$ metabolism in the kidneys but not elsewhere in the body.

Example 2

In this example, a metabolite of clioquinol was synthesized. It is known that the clioquinol is excreted through the kidneys as glucuronide derivatives of clioquinol (Kotaki et al.: "Enterohepatic circulation of clioquinol in the rat", *J. Pharmacobiodyn.* 1984 June; 7(6):420-5 and Jurima et al.: "Metabolism of 14C-iodochlorhydroxy-quinoline in the dog and the rat", *J. Pharmacobiodyn.* 1984 March; 7(3):164-70). The transformation of clioquinol to the corresponding glucuronide presumably takes place in the liver. Following the formation of clioquinol glucuronide in the liver, it is eventually transferred to the kidneys for excretion in the urine.

A glucuronide derivative of clioquinol in the form of methyl(5-chloro-7-iodo-quinolyl-2',3',4'-tri-O-acetylglycopyranosid)uronate was prepared according to the following reaction scheme:

A mixture of 5-chloro-8-hydroxy-7-iodo-quinoline (50 mg, 0.164 mmol), methyl 1-bromo-1-deoxy-2,3,4-tri-O-acetyl-D-glucopyranosiduronate (65 mg, 0.164 mmol), $CaSO_4.H_2O$ (35 mg) and pyridine (1.5 ml) was stirred at room temperature for 20 min. Freshly prepared $Ag_2CO_3$ (35 mg) was added to the reaction mixture and the suspended solution was stirred at room temperature for 20 hours in the dark. Subsequently, the reaction product was deacetylated by 1N aqueous NaOH.

The reaction mixture was diluted with $CH_2Cl_2$ (10 ml), filtered and the solvent evaporated under reduced pressure. The above product was purified by flash chromatography (TLC: $CH_2Cl_2$/MeOH 99/1, eluent: $CH_2Cl_2$/.MeOH 99.5/0.5).

NMR (400 MHz, $CDCl_3$) 2.04 (s, 3H, Ac), 2.09 (s, 3H, Ac), 2.13 (s, 3H, Ac), 3.68 (s, 3H, Me), 3.99 (d, 1H, 5' H), 5.40–5.52 (m, 3H, 2', –3', –4'-H), 6.29 (d, 1H, 1' -H), 7.56 (m, 1H, 3H), 7.99 (s, 1H, 6-H), 8.52 (d, 1H, 4-H), 8.93 (s, 1H, 2-H).

This compound is referred to as clioquinol glucuronide in the following.

Example 3

The interaction of vitamin $B_{12}$ with clioquinol glucuronide as prepared in example 2, was studied using nuclear magnetic resonance (NMR) spectroscopy.

As the clioquinol glucuronide is soluble in water, the study was undertaken in buffered water at PH=6.5. Three different solutions were prepared and their $^1H$ NMR spectra were recorded in a DRX 400 MHz spectrophotometer at 20° C. Solution a) contained free vitamin $B_{12}$ (hydroxycobalamin) in a concentration of 2.6 mM. Solution b) contained a mixture of 2.6 mM vitamin $B_{12}$ and 10 mM clioquinol glucuronide (mole ratio of about 1:4). Solution c) contained 10 mM clioquinol glucuronide.

Figure 1A:
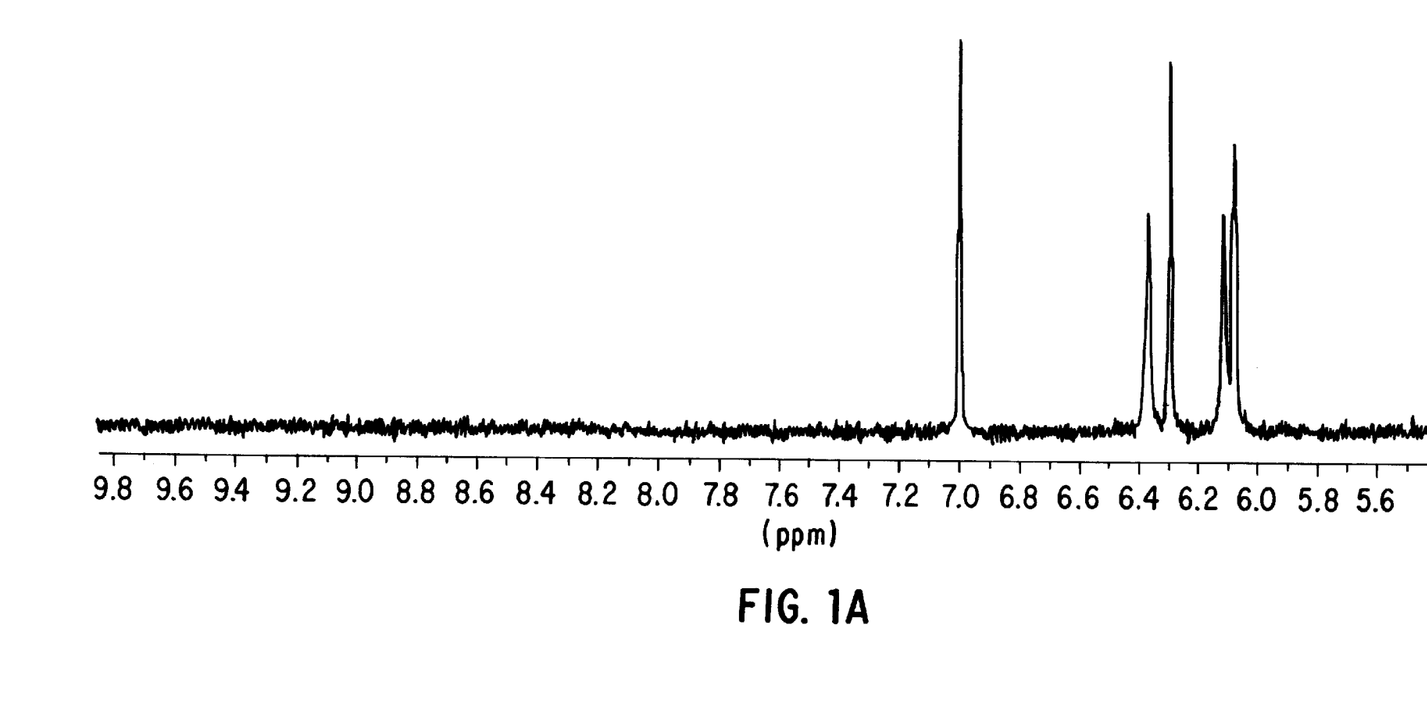
FIGS. 1A–1C depicts the NMR spectra of three solutions. Solution a contained vitamin $B_{12}$ (hydroxycobalamin), at a concentration of 2.6 mM. Solution b contained a mixture of 2.6 mM vitamin $B_{12}$ and 10 mM clioquinol glucuronide (mole ratio of about 1:4). Solution c contained 10 mm clioquinol glucuronide.
Figure 1B:
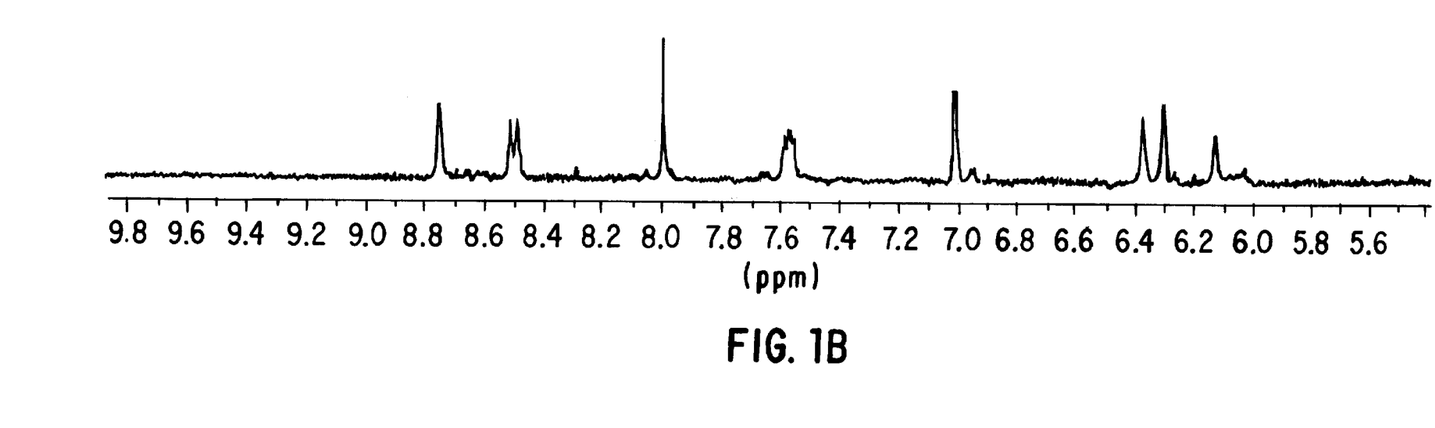
Figure 1C:
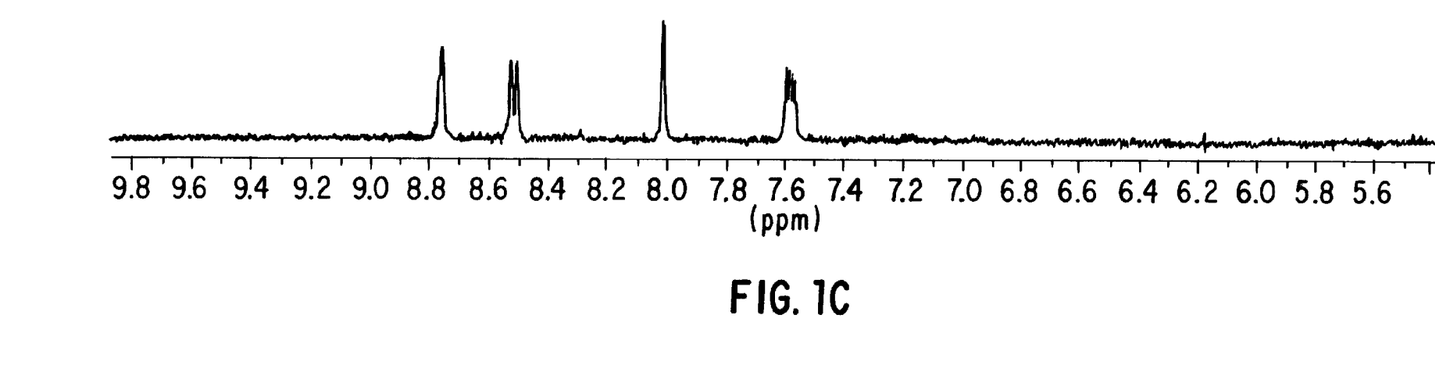
Figure 2A:
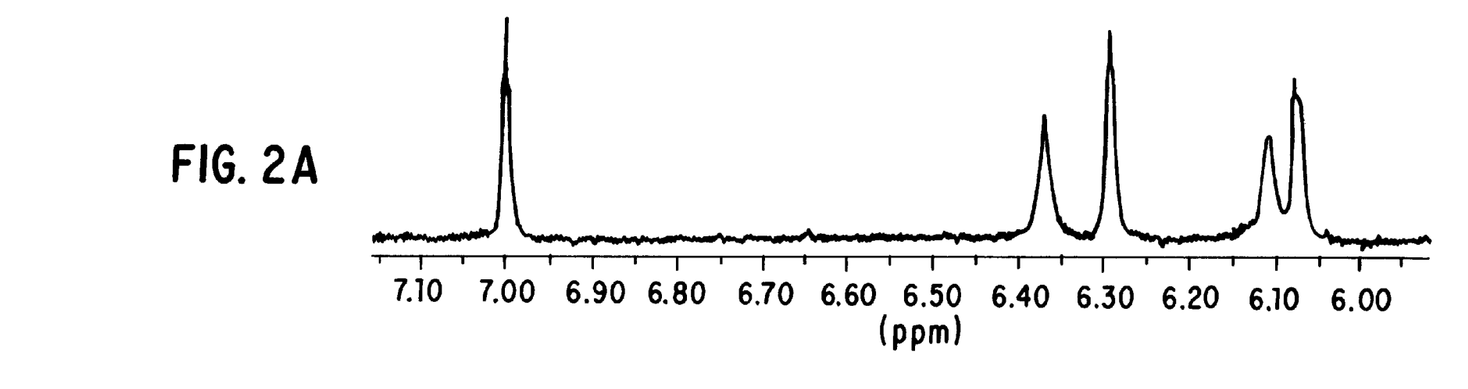
FIGS. 2A–2C depicts the right half of FIGS. 1A–1C expanded for easier comparison of the resonance positions.
Figure 2B:
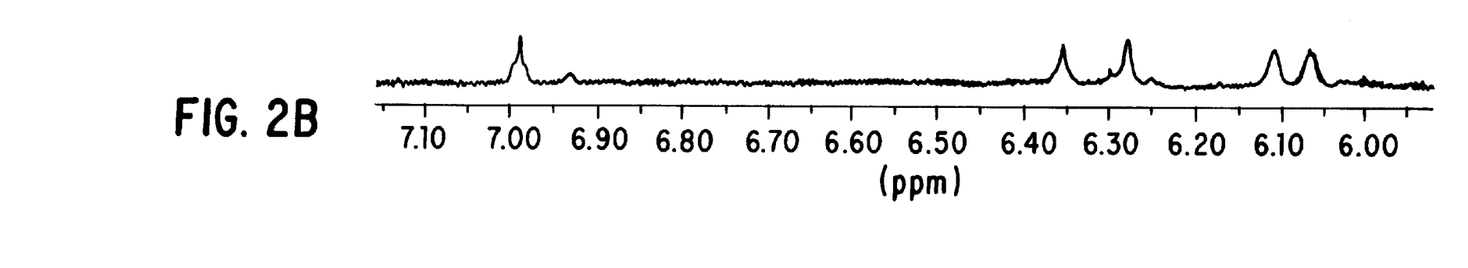
Figure 2C:
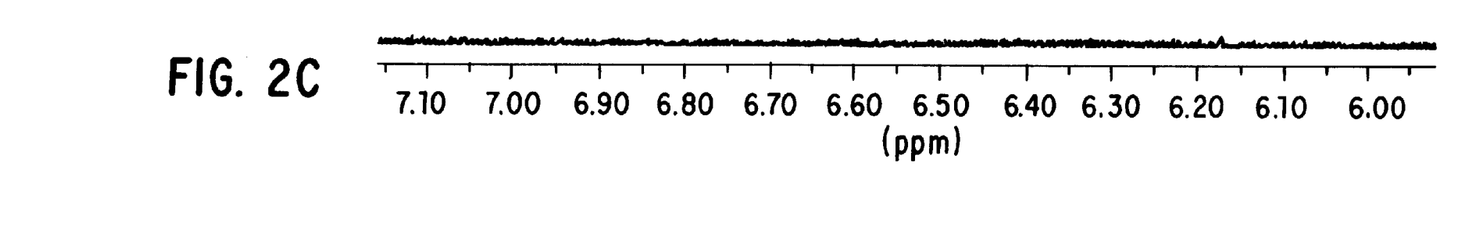
Figure 3B:
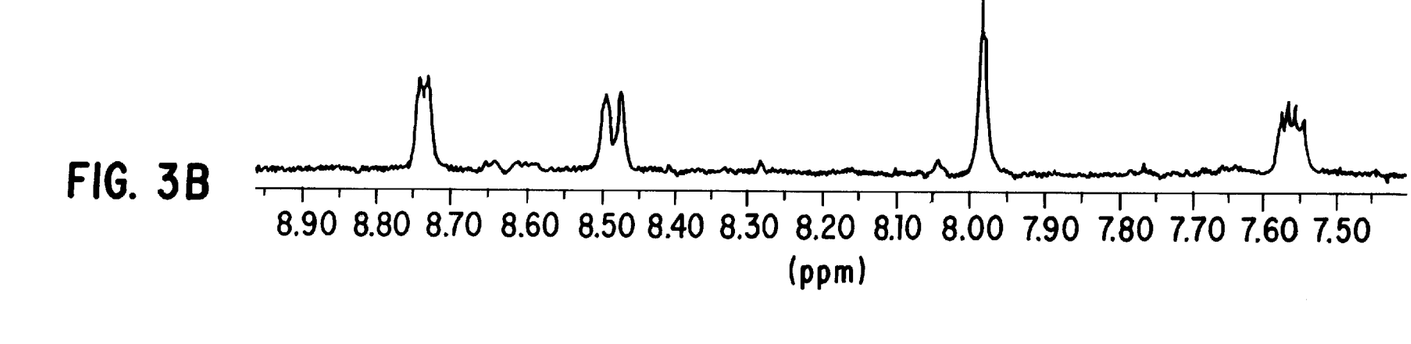
FIGS. 3B–3C depicts the left half of FIGS. 1B–1C expanded for easier comparison of the resonance positions.
Figure 3C:
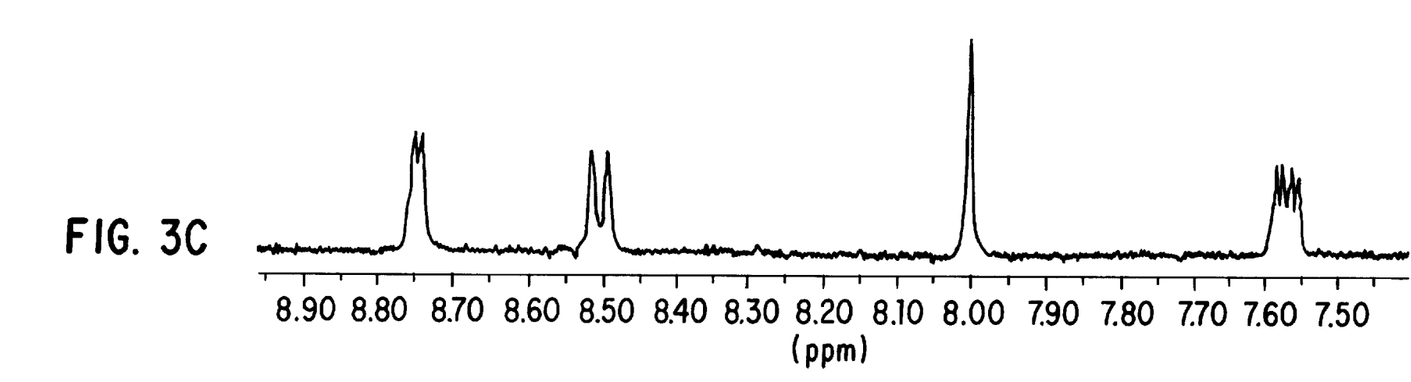

In FIGS. 1A–1C the spectra of the three solutions a, b and c are presented for the aromatic region (5.5–9.8 ppm). The differences are quite small but obvious in the expansion shown of FIGS. 2A–2C and FIGS. 3B–3C respectively. Some of the resonances of vitamin $B_{12}$ (corresponding to the benzimidazole moiety) have shifted (see FIGS. 2A–2B) and the same is observed for two resonances of the clioquinol glucuronide (corresponding to the quinoline moiety) (see FIGS. 3B–3C).

The results suggest an interaction between clioquinol glucuronide and vitamin $B_{12}$, possibly of a hydrophobic nature between the benzimidazole moiety of the vitamin $B_{12}$ and the quinoline moiety of clioquinol glucuronide.

The hydrophobic binding of vitamin $B_{12}$ to clioquinol glucuronide is believed to cause the vitamin $B_{12}$ to be excreted from the body together with clioquinol glucuronide, thus preventing resorption of vitamin $B_{12}$, which would eventually lead to a vitamin $B_{12}$ deficiency. Therefore, vitamin $B_{12}$ deficiency is believed to be, at least to some extent, the underlying cause of SMON.

Example 4

Preparation of a pharmaceutical composition comprising clioquinol and vitamin $B_{12}$.

250 g of clioquinol (5-chloro-7-8-quinoline) was mixed for a period 3 minutes with 1657.5 g micro crystalline cellulose and 20 g sodium lauryl sulphate. An aqueous solution of 25 g polyvidone and an aqueous solution of 5.0 g vitamin $B_{12}$ (cyanocobalamine) was added to the clioquinol containing powder mixture under stirring. This mixture was passed through granulating sieves (2.5 mm) and desiccated for a period of 20 hours at 40° C. The dry mixture (sieved at 1.25 mm) was blended with 30 g sodium lauryl sulphate and 12.5 g magnesium stearate. This mixture was formed into tablets having a diameter of 8.0 mm and a weight of 200 mg.

Example 5

Preparation of a pharmaceutical composition comprising clioquinol and vitamin $B_{12}$.

250 g of clioquinol (5-chloro-7-iodo-8-quinoline) was mixed with 200 g sapamines (N-(4'-stearoylamino-phenyl) trimethylammonium methyl sulfuric acid) and 1025 g lactose mono hydrate for a period of 5 minutes. 300 g of boiling water was added to a mixture of 100 g maize starch in 100 g cold water. The maize suspension, cooled to 40° C. was added to the clioquinol containing powder mixture under continuous stirring. Subsequently, an aqueous solution of 5 g vitamin $B_{12}$ was added. The mixture was granulated using a 2.5 mm sieve and desiccated for 18 hours at 40° C. The dry granules were mixed with 400 g maize starch and 20 g magnesium stearate. The final mixture was formulated into tablets having a diameter of 8.0 mm and a weight of 200 mg.

Example 6

The resolubilization of amyloid aggregates by clioquinol was studied. 5.3 g of clioquinol was suspended with agitation in 200 ml of n-decane. The undissolved material was allowed to settle. Weighing the dried undissolved clioquinol after blowing off the decane indicated that only 2% of the clioquinol dissolved in the decane. 100 ml of the (light yellow) supernatant was agitated together with 100 ml of PBS pH 7.4 and the phases allowed to separate. The PBS (lower phase) was collected and filtered to remove the residue which formed at the phase interface upon extraction with the organic solvent. Assuming that 2% of the clioquinol dissolved in the n-decane, and assuming that the partitioning coefficient is 1/1750 with PBS at 1:1 mixtures of decane/clioquinol, the concentration of clioquinol in the PBS is 800 nM.

Brain specimens were obtained for which a histopathological diagnosis of Alzheimer's disease was confirmed. Duplicate 0.5 g specimens of frontal lobe neocortex were homogenized in 3 ml of the clioquinol/PBS solution at 100%, 10% and 1% of the final PBS/clioquinol extract and PBS alone.

The homogenates were centrifuged at 150,000 xg for thirty minutes and the supernatants collected and held on ice (fraction "S"). The pellets were subjected to an identical homogenization and centrifugation regime and the resulting supernatants again collected (fraction "P").

1 ml of each supernatant was treated with 200 µl of ice cold 10% TCA to precipitate total protein including Aβ. The resulting pellet was washed once with 100% ethanol and resuspended in 100 µl of TBS (tris 20 mM, NaCl 150 mM, pH 7.4).

7.5 µl of sample (S or P) was boiled for 5 min. with an equal volume of tris-tricine sample buffer containing 4% SDS and loaded onto a Novex pre-cast 10–20% tris-tricine gel followed by Western transfer onto nitrocellulose. Signal for Aβ was detected using mAb WO2 (raised against residues 5–16 of Aβ) and visualized using ECL. The sensitivity of the detection system is 5–10 pg.

To validate the TCA precipitation for Aβ 1 µg of synthetic Aβ 1–40 was added to 1 ml of PBS containing 10% BSA and the solution was treated as above. Signal for Aβ was detected in the precipitated pellet but not in the supernatant.

Figure 4:
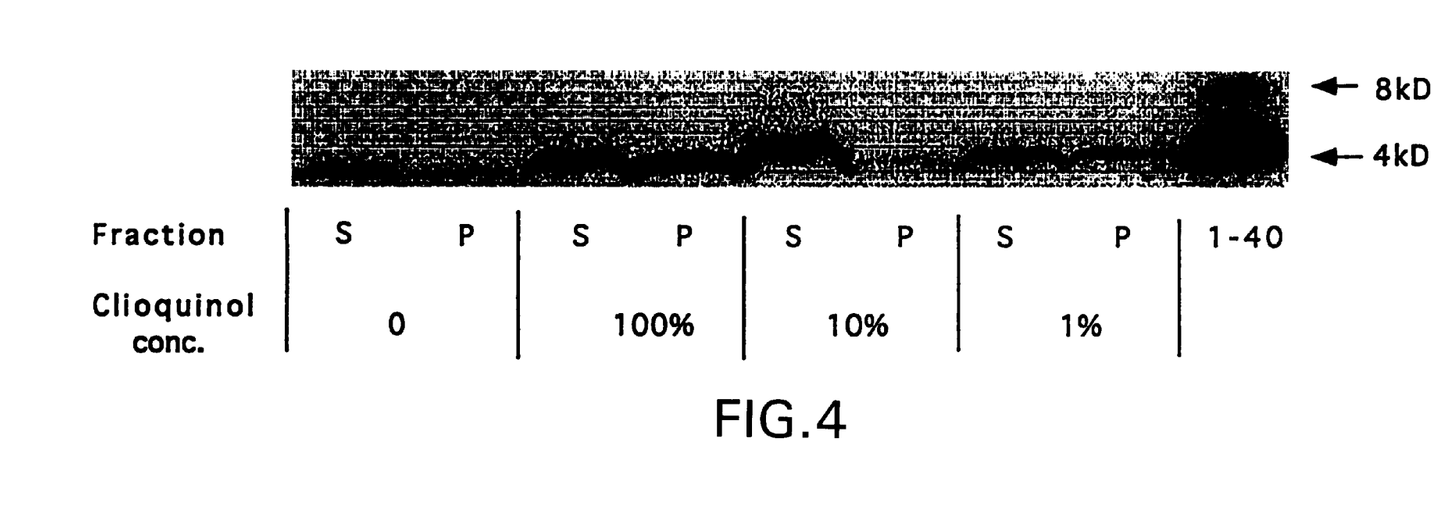
FIG. 4 depicts the amounts of β amyloid found in the supernatants of brain specimen homogenates taken from patients diagnosed with Alzheimer's disease after the homogenates were exposed to several concentrations of clioquinol (100%=800 nM clioquinol). The lane labeled "1–40" contains TCA precipitated synthetic Aβ.

The result is indicated in FIG. 4.

As can be deduced from FIG. 4, the clioquinol was effective in promoting the solubilization of Aβ in the concentrations tested. Furthermore, the optimal concentration was found to be "10%", indicating that one of the aggregation forms of Aβ, presumably the dimer, is more soluble in PBS than others.

While data are shown only for one specimen in FIG. 4, data for 19 other specimens all indicate the same tendency, viz. that clioquinol is effective in promoting the solubilization of Aβ.

Example 7

A comparison of the chelating abilities of EDTA and clioquinol was made. Samples of 10 ng synthetic Aβ were placed in microtitre wells and caused to aggregate by the addition of 25 µM ZnCl. The aggregates were then transferred to a 0.2 µm nylon membrane by filtration. The aggregates were washed with 200 µl TBS alone, TBS containing 2 µM EDTA, and TBS containing 2 µM clioquinol. The membrane was fixed, probed with the anti Aβ monoclonal antibody 6E10 and developed for exposure to ECL-film. The transmittance of the ECL-film was measured and the relative signal strength calculated based on 100% for TBS alone. The relative signal strength was 66% for EDTA and 49% for clioquinol.

The results indicate that clioquinol is a better chelator for zinc precipitated Aβ than EDTA.

Example 8

The ability of clioquinol to resolubilize zinc-aggregated Aβ was assessed. A 2.5 µM solution of Aβ in TBS at a pH of 7.4 was prepared. 95% of the Aβ was maintained in a soluble state. Addition of 30 µM zinc resulted in precipitation of the soluble Aβ and only 43% was maintained in solution. The subsequent addition of 120 µM clioquinol to the zinc precipitated Aβ resulted in an increase of soluble Aβ to 70%.

The results indicate that clioquinol is able to redissolve zinc precipitated Aβ.

Example 9

A patient suffering from Alzheimer's disease is treated with the tablet described in Example 5 as follows:

In the first period of treatment, one tablet a day for two weeks is administered, followed by a two week wash-out period, during which vitamin $B_{12}$ administration alone is continued. The tablet containing vitamin $B_{12}$ alone is formulated identically to the tablet described in Example 5, except that clioquinol is omitted. After the wash-out period, the first period is repeated. During the treatment, the amount of solubilized Aβ in the patient's cerebrospinal fluid (CSF) is monitored. If there is no increase in solubilized Aβ in response to the clioquinol administration, indicative of resolubilization of zinc-Aβ aggregates, the dosage is raised to two tablets once a day. An observed increase of solubilized Aβ in the patient's CSF indicates that the treatment is effective at resolubilizing Aβ. Preferably, two more cycles of clioquinol in combination with vitamin $B_{12}$ followed by vitamin $B_{12}$ alone are administered.

Various publications are cited herein, the disclosures of which are incorporated by reference in their entireties.

The invention being thus described, it will be obvious that the same may be varied in many ways. Such variations are not to be regarded as a departure from the spirit and scope of the invention, and all such modifications, as would be obvious to a person skilled in the art, are intended to be included in the scope of the following claims.

What is claimed is:

1. A pharmaceutical composition comprising a therapeutically effective amount of clioquinol and vitamin $B_{12}$.

2. The pharmaceutical composition according to claim 1, which further comprises a pharmaceutically acceptable carrier.

3. The pharmaceutical composition according to claim 1, wherein the amount of clioquinol is 5 to 250 mg.

4. The pharmaceutical composition according to claim 1, wherein the amount of clioquinol is 10 to 50 mg.

5. The pharmaceutical composition according to claim 1, wherein the amount of vitamin $B_{12}$ is 5 µg to 2 mg.

6. The pharmaceutical composition according to claim 3, wherein the amount of vitamin $B_{12}$ is 5 µg to 2 mg.

7. The pharmaceutical composition according to claim 1, wherein the amount of vitamin $B_{12}$ is 0.5 mg to 1 mg.

8. The pharmaceutical composition according to claim 1, wherein the composition is formulated for parenteral or intradermal administration.

9. The pharmaceutical composition according to claim 1, wherein the composition is formulated for oral administration.

10. The pharmaceutical composition according to claim 1, 2, or 3, wherein the pharmaceutical composition is formulated as a pill.

11. The pharmaceutical composition according to claim 1, 2, or 3, wherein the pharmaceutical composition is formulated as a tablet.

12. The pharmaceutical composition according to claim 1, 2, or 3, wherein the pharmaceutical composition is formulated as a capsule.

13. The pharmaceutical composition according to claim 1, 2, or 3, wherein the pharmaceutical composition is formulated as a suppository.

14. The pharmaceutical composition according to claim 1, 2, or 3, wherein the pharmaceutical composition is formulated for oral administration with an emulsifying agent.

15. The pharmaceutical composition according to claim 14, wherein the emulsifying agent is N-(4'-stearoylaminophenyl)-trimethylammonium methyl sulfuric acid.

16. The pharmaceutical composition according to claim 1, 2, or 3, wherein the clioquinol and vitamin $B_{12}$ are each purified.

17. The pharmaceutical composition of claim 12, wherein the clioquinol and vitamin $B_{12}$ are each purified.

18. A kit comprising in one or more containers a therapeutically effective amount of clioquinol, and an amount of vitamin $B_{12}$ effective to inhibit a detrimental side effect of clioquinol administration.

19. A method of treating a subject with a disease or disorder responsive to clioquinol administration comprising administering to the subject clioquinol and vitamin $B_{12}$.

20. A method of treating a subject having or suspected of having a disease or disorder responsive to clioquinol administration while inhibiting detrimental side effects comprising administering to the subject (a) a therapeutically effective amount of clioquinol, and (b) an amount of vitamin $B_{12}$ effective to inhibit a detrimental side effect of clioquinol administration.

21. The method according to claim 20 wherein the clioquinol and vitamin $B_{12}$ are comprised in a single pharmaceutical composition.

22. The method according to claim 20 wherein the clioquinol and vitamin $B_{12}$ are administered sequentially.

23. The method according to claim 20 wherein the clioquinol and vitamin $B_{12}$ are administered substantially simultaneously.

24. The method according to claim 22 wherein a pharmaceutical composition comprising clioquinol is administered for one to three weeks, followed by a period of one to four weeks during which a pharmaceutical composition comprising vitamin $B_{12}$ is administered and clioquinol is not administered.

25. The method according to claim 20 wherein the subject is human.

26. The method according to claim 25 wherein the disease or disorder is Alzheimer's disease.

27. The method according to claim 25 wherein the disease or disorder is Parkinson's disease.

28. The method according to claim 25 wherein the disease or disorder is a bacterial, protozoal, viral or fungal infection.

29. The method according to claim 25 wherein the disease or disorder is an infection by Helicobacter pylori.

30. The method according to claim 25 wherein the disease or disorder is caused by rota-virus.

31. The method according to claim 20 wherein the clioquinol and vitamin $B_{12}$ are administered orally.

32. The method according to claim 21 wherein the pharmaceutical composition is a capsule.

33. The method according to claim 20, 21 or 32 wherein the clioquinol and vitamin $B_{12}$ are each purified.

* * * * *